United States Patent
Mari et al.

(10) Patent No.: US 10,322,216 B2
(45) Date of Patent: Jun. 18, 2019

(54) FILTERING DEVICE

(71) Applicant: Fresenius HemoCare Italia Srl, Cavezzo (IT)

(72) Inventors: Giorgio Mari, Mirandola (IT); Serena Borghi, Medolla (IT); Elena Finetti, Mirandola (IT)

(73) Assignee: Fresenius Hemocare Italia S.R.L., Cavezzo (IT)

( * ) Notice: Subject to any disclaimer, the term of this patent is extended or adjusted under 35 U.S.C. 154(b) by 0 days.

(21) Appl. No.: 15/109,074

(22) PCT Filed: Dec. 17, 2014

(86) PCT No.: PCT/EP2014/078119
§ 371 (c)(1),
(2) Date: Jun. 29, 2016

(87) PCT Pub. No.: WO2015/113699
PCT Pub. Date: Aug. 6, 2015

(65) Prior Publication Data
US 2016/0325029 A1    Nov. 10, 2016

(30) Foreign Application Priority Data

Jan. 30, 2014 (EP) .................................. 14153244

(51) Int. Cl.
*A61M 1/02* (2006.01)
*B01J 20/28* (2006.01)
(Continued)

(52) U.S. Cl.
CPC ........... *A61M 1/0281* (2013.01); *A61K 35/14* (2013.01); *A61M 1/362* (2014.02);
(Continued)

(58) Field of Classification Search
CPC combination set(s) only.
See application file for complete search history.

(56) References Cited

U.S. PATENT DOCUMENTS

| | | | |
|---|---|---|---|
| 2002/0159995 A1 | 10/2002 | Brady et al. | |
| 2003/0003438 A1* | 1/2003 | Hirai | ................... A61M 1/3472 435/4 |

FOREIGN PATENT DOCUMENTS

| | | |
|---|---|---|
| EP | 0 320 194 A1 | 6/1989 |
| EP | 0 424 698 A1 | 5/1991 |

(Continued)

OTHER PUBLICATIONS

Grimshaw, et al., "New frontiers in transfusion biology: Identification and significance of mediators of morbidity and mortality in stored red cell concentrates," (2001), April 51(4), pp. 874-880.

(Continued)

*Primary Examiner* — Dirk R Bass
(74) *Attorney, Agent, or Firm* — Cook Alex Ltd.

(57) ABSTRACT

The present invention relates to a filtering device (8) for removing substances from blood or a blood component, the filtering device (8) comprising: a housing having an inlet and an outlet, at first sorbent material coupled with at least a first ligand located within the housing, and a second sorbent material coupled with at least a second ligand located within the housing, wherein the first ligand is for removing free hemoglobin (fHb) and the second ligand is for removing microvesicles (MV) from the blood or blood component passing through the filtering device (8), from the inlet to the outlet, wherein the first and second ligand are different from each other, and wherein the first and second sorbent material are the same or are different from each other.

32 Claims, 1 Drawing Sheet

(51) Int. Cl.
*A61M 1/36* (2006.01)
*A61K 35/14* (2015.01)
*B01D 15/26* (2006.01)
*B01J 20/26* (2006.01)
*B01J 20/30* (2006.01)
*B01D 15/00* (2006.01)
*B01J 20/32* (2006.01)

(52) U.S. Cl.
CPC ........ *A61M 1/3633* (2013.01); *A61M 1/3679* (2013.01); *B01D 15/00* (2013.01); *B01D 15/26* (2013.01); *B01J 20/267* (2013.01); *B01J 20/28016* (2013.01); *B01J 20/28052* (2013.01); *B01J 20/28085* (2013.01); *B01J 20/3085* (2013.01); *B01J 20/321* (2013.01); *B01J 20/327* (2013.01); *B01J 20/3248* (2013.01); *B01J 20/3285* (2013.01); *B01J 2220/445* (2013.01); *B01J 2220/603* (2013.01)

(56) References Cited

FOREIGN PATENT DOCUMENTS

| EP | 2 012 118 A1 | 1/2009 |
|----|--------------|--------|
| EP | 2 495 025 A1 | 9/2012 |
| WO | WO 95/13125 A1 | 5/1995 |
| WO | WO 01/59455 A2 | 8/2001 |
| WO | WO 2007/103572 A2 | 9/2007 |
| WO | WO 2012/094565 A1 | 7/2012 |
| WO | WO 2014/012168 A1 | 1/2014 |

OTHER PUBLICATIONS

International Search Report for International Application No. PCT/EP2014/078119, dated Oct. 4, 2013.

Written Opinion of the International Searching Authority for International Application No. PCT/EP2014/078119, dated Oct. 4, 2013.

Cardigan, R. and Smith, K., Evaluation of the HemoCue Plasma Haemoglobin Analyser for Assessing Haemolysis in Red Cell Concentrates During Storage, Vox Sanguinis, 2002, vol. 82, pp. 76-79.

Okay, O., Macroporous Copolymer Networks, Progress in Polymer Science, 2000, vol. 25, pp. 711-779.

Rubin, O., et al., Microparticles in Stored Red Blood Cells: An Approach Using Flow Cytometry and Proteomic Tools, Vox Sanguinis, 2008, vol. 95, pp. 288-297.

Sherrington, D.C., Preparation, Structure, and Morphology of Polymer Supports, Chemical Communications, 1998, vol. 21, pp. 2275-2286.

Xiong, Z., et al., Red Cell Microparticle Enumeration: Validation of a Flow Cytometric Approach, Vox Sanguinis, Jul. 2012, vol. 103(1), pp. 42-48, doi: 10.1111/j.1423-0410.2011.01577.x.

* cited by examiner

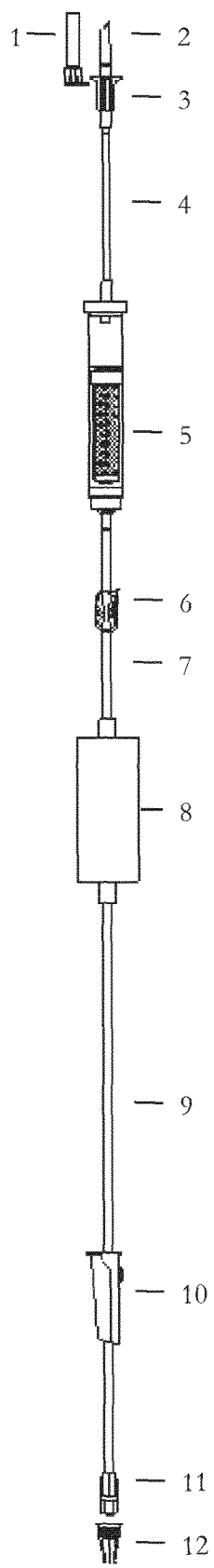

FILTERING DEVICE

CROSS-REFERENCE TO RELATED APPLICATIONS

This is a U.S. national stage application of International Patent Application No. PCT/EP2014/078119, filed Dec. 17, 2014, which claims the benefit of and priority to EP Application Serial No. 14153244.0, filed Jan. 30, 2014, both of which are incorporated herein by reference.

FIELD OF THE INVENTION

The present invention relates to a filtering device (8) for removing substances from blood or a blood component, the filtering device (8) comprising: a housing having an inlet and an outlet, at first sorbent material coupled with at least a first ligand located within the housing, and a second sorbent material coupled with at least a second ligand located within the housing, wherein the first ligand is for removing free hemoglobin (fHb) and the second ligand is for removing microvesicles (MV) from the blood or blood component passing through the filtering device (8), from the inlet to the outlet, wherein the first and second ligand are different from each other, and wherein the first and second sorbent material are the same or are different from each other.

BACKGROUND OF THE INVENTION

Although red blood cell transfusions can be lifesaving, they are not without risk. In critically ill patients, red blood cell transfusions are associated with increased morbidity and mortality, which may increase with prolonged red blood cell storage before transfusion.

Recent studies support a growing appreciation that hemolysis represents one fundamental mechanism associated with increased mortality and morbidity after receipt of red blood cell transfusions.

This concept evolved from clinical trial observations suggesting that trauma patients receiving hemoglobin-based oxygen carriers developed hypertension and multi-organ injury caused by hemoglobin-NO-scavenging-reactions, and clinical observations of vasculopathy complications in patients with hemoglobinopathies and hemolytic anaemia.

Hemolysis represents a problem encountered with red blood cell transfusions, in particular upon prolonged storage prior to use. Hemolysis results in the release of free hemoglobin (fHb). fHb is a source of heme, which in turn can contribute to increased damage caused by reactive oxygen species.

Aerobic organisms are well endowed with enzymatic oxidant defence systems, which provide protection against activated oxygen species. However, damages caused by reactive oxygen can be greatly amplified by redox-active iron. One abundant source of potentially toxic redox-active iron is heme, and both exogenous and endogenous heme can synergistically enhance oxidant mediated cellular damage.

Heme is quite hydrophobic, readily enters cell membranes, and greatly increases cellular susceptibility to oxidant-mediated killing. Heme also acts as a catalyst for the oxidation of low-density lipoprotein (LDL), generating products toxic to endothelia.

The toxic effects of heme may be important in a number of pathologies. These include not only acute conditions such as intravascular hemolysis (which can lead to renal failure) but also more insidious processes such as atherogenesis, in which intra-lesional deposits of iron (perhaps derived from erythrocytes, which are known to intrude into atherosclerotic lesions) have been observed.

Free hemoglobin in plasma, when oxidized, can provide heme to endothelia, which greatly enhances cellular susceptibility to oxidant-mediated cell injury.

A second factor contributing to adverse effects observed in relation with red blood cell transfusions are so called microvesicles (MV). MV, also described as ectosomes, are populations of phospholipid vesicles of 1 µm or less, released into the blood by erythrocytes, platelets, white blood cells or endothelial cells. The production of MV is a highly controlled process, triggered by various stimuli, including cell stimulation and apoptosis. If MV have been first described as cell dusts, they are now recognized as being involved in a broad spectrum of biological activities, such as thrombosis and hemostasis, inflammation, vascular and immune function, apoptosis or even intercellular communication by the transfer of surface proteins.

While MV also can be detected in healthy individuals, their increase has been observed in a variety of diseases with elevated thrombotic risk, vascular involvement or metastasis.

Typically, blood products such as blood or blood components (e.g. red blood cells, platelets, plasma) undergo further treatment and storage prior to their administration to a subject in need thereof. It has been known that the quality of blood or blood components may decrease with increased storage times. In particular, the concentration of fHb and MV in the blood product increases with increasing storage time.

In particular, under blood bank conditions, red blood cells undergo progressive structural and biochemical changes commonly referred to as "the storage lesion". Red blood cells (also designated as erythrocytes) show progressive cell shape transformation from biconcave disk to rigid spheroechinocyte, accompanied by the release of MV from the tips of spicules and their accumulation in the blood product. In addition, there is a depletion of ATP, pH acidification, and hemolysis, the hemolysis resulting in the accumulation of fHb.

Red blood cell membrane modification during storage is triggered by ATP depletion and oxidation and is centred on changes in band 3, leading to membrane detachment and disorganization that probably affect red blood cell deformability, osmotic resistance and survival after transfusion.

Red blood cell MV formation represents a continuous process of membrane remodelling, which occurs early during blood banking, and prevents the exposure of phosphatidylserine on red blood cells. MV found in red blood cell concentrates generally originate from red blood cells and their number gradually increases with storage time.

However, there is an increasing demand for blood products, while the blood supply by donors is fluctuating, resulting in the periodical shortage of blood products. Thus, improving the quality and safety of stored blood products is important to address the increasing demand.

Therefore, it is highly desirable to reduce the content of fHb and MY in blood products such as whole blood or blood components, in particular those comprising red blood cells, prior to their administration to a subject in need thereof. This would improve safety and quality of the blood product, also after prolonged storage times.

Attempts have been made to "wash" blood or blood components, in particular those comprising red blood cells, after storage and prior to administration, in order to remove cellular debris and undesired substances from the stored blood product. To that end, attempts have been made to resuspend red blood cells in saline, followed by centrifugation and separation from the supernatant. However, this method is very time consuming and expensive, because it must be performed under sterile conditions in order to avoid the risk of infection for the recipient.

On the other hand, methods aiming to slow down the development of storage lesions (e.g. by storage of red blood cell containing blood products under anaerobic conditions) require the treatment of all blood products already after blood collection and therefore, prior to storage of the product. Thus, this approach does not allow selective treatment of only those blood products requiring said treatment due to prolonged storage. Instead, all blood products are treated, irrespective of storage time. This again results in increased cost and may also result in prolonged handling times.

Thus, there is a need for methods and devices for improving the quality and safety of stored blood products, in particular products comprising red blood cells, prior to their administration to a subject in need thereof.

SUMMARY OF THE INVENTION

According to one embodiment of the invention, a filtering device (8) for removing substances from blood or a blood component is provided, the filtering device (8) comprising: a housing having an inlet and an outlet, at first sorbent material coupled with at least a first ligand located within the housing, and a second sorbent material coupled with at least a second ligand located within the housing, wherein the first ligand is for removing free hemoglobin (fHb) and the second ligand is for removing microvesicles (MV) from the blood or blood component passing through the filtering device (8), from the inlet to the outlet, wherein the first and second ligand are different from each other, and wherein the first and second sorbent material are the same or are different from each other.

Optionally, the first sorbent material is not coupled with the second ligand and the second sorbent material is not coupled with the first ligand.

The first and/or second sorbent material can comprise a polymer, wherein the polymer comprises polymethacrylate, polyacrylamide, polystyrene-divinylbenzene, or a combination or co-polymer thereof. A preferred polymer is a polymer comprising polymethacrylate.

The first ligand for removing fHb can comprise polyacrylic acid, polyacrylic ester or a combination or co-polymer thereof.

The second ligand for removing MV can comprise at least one R—$NH_2$ group, wherein R is (—$CH_2$—)$_n$, wherein n is 1-5, preferably 1-3, more preferably 1-2. The first sorbent material can be coupled with the at least first ligand by a binding reaction, and/or the second sorbent material can be coupled with the at least second ligand by a binding reaction.

The first and/or second sorbent material can be selected from the group consisting of beads and fibers.

The beads can have a particle diameter of about 100 µm to about 400 µm, such as about 100 µm to about 200 µm.

The beads can comprise pores, the pores having a pore size of about 50 nm to about 100 nm.

Thus, the beads can have a particle diameter of about 100 µm to about 200 µm, and/or comprise pores, the pores having a pore size of about 50 nm to about 100 nm. Also, the beads can have a particle diameter of about 100 µm to about 400 µm, and/or comprise pores, the pores having a pore size of about 50 nm to about 100 nm.

The filtering device (8) can comprise a first sorbent material that is beads having a particle diameter of about 100 µm to about 200 µm, and comprising pores having a pore size of about 50 nm to about 100 nm. Alternatively or in addition, the filtering device (8) can comprise a second sorbent material that is beads having a particle diameter of about 100 µm to about 400 µm, and comprising pores, the pores having a pore size of about 50 nm to about 100 nm.

The first sorbent material and the second sorbent material can be provided within the housing at a ratio (volume: volume) of about 1 to about 2.

The first sorbent material can form at least one layer within the housing, and the second sorbent material can form at least one layer within the housing. The layers formed by the first and second sorbent materials can be stacked.

The first sorbent material and the second sorbent material can be substantially equally dispersed within the housing.

The filtering device (8) can be adapted for integration into a blood transfusion system, and/or the filtering device (8) can be connectable to a container comprising blood or a blood component.

The housing of the filtering device (8) can have a length and a diameter, wherein the ratio of length:diameter is about 2 to about 4, preferably about 2 to about 3, more preferably about 3, optionally wherein the housing is a column, or is a cartridge.

The filtering device (8) can further comprise a net located within the housing, the net accommodating the first and/or second sorbent material, the net being adapted for entrapping and/or removing from the housing the first and second sorbent material.

The blood component to be filtered can comprise red blood cells, preferably wherein the blood component is red cell concentrate (RCC).

According to a further embodiment, a blood transfusion system comprising at least one filtering device (8) according to the invention is provided.

One embodiment according to the present invention provides for the use of the filtering device (8) according to the invention for the removal of substances, such as fHb and MV, from blood and/or blood components.

Also, according to a further embodiment, a method for removing substances ex vivo from blood or a blood component is provided, the method comprising the steps: (a) providing a filtering device (8) according to the invention or a blood transfusion system according to the invention, and (b) allowing the blood or blood component to pass through the filtering device (8), from the inlet to the outlet.

The blood component subjected to a method according to the invention can comprise red blood cells, preferably wherein the blood component is red cell concentrate (RCC).

The blood or blood component subjected to a method according to the invention can be stored blood or a stored blood component. Thus, the blood or blood component can be stored prior to filtration.

According to still a further embodiment, a kit is provided, the kit comprising: a first filtering device (8) for removing substances from blood or a blood component, the first filtering device (8) comprising a housing having an inlet and an outlet, and at least a first sorbent material located within the housing, wherein the first sorbent material is coupled with at least a first ligand for removing fHb from the blood or blood component passing through the first filtering device (8), from the inlet to the outlet, and a second filtering device (8) for removing substances from blood or a blood component, the second filtering device (8) comprising a housing having an inlet and an outlet, and at least a second sorbent material located within the housing, wherein the second sorbent material is coupled with at least a second ligand for removing MV from the blood or blood component passing through the second filtering device (8), from the inlet to the outlet, wherein the first and second ligand are different from each other, and wherein the first and second sorbent material are the same or are different from each other. Optionally, the first sorbent material is not coupled with the second ligand and the second sorbent material is not coupled with the first ligand.

The first and/or second filtering device (8) can be adapted for integration into a blood transfusion system. The first and/or second filtering device (8) can be connectable to a container comprising blood or a blood component.

The first filtering device (8) and the second filtering device (8) can be integrated in a blood transfusion system and can be connectable to a container comprising blood or a blood component.

The filtering device (8) according to the present invention can be a filtering device (8) wherein the first and/or second sorbent material comprises or consists of beads, wherein further the beads are immobilized. The immobilization can be effected by sinterization or by agglomeration. The immobilized beads can be placed in the housing of the filtering device (8).

SHORT DESCRIPTION OF THE FIGURE

FIG. 1 shows an example of a blood transfusion system according to the invention.

DEFINITIONS

The patent and scientific literature referred to herein establishes knowledge that is available to those of skill in the art. The patent and scientific literature referred to herein is hereby incorporated by reference to the same extent as if each was specifically and individually indicated to be incorporated by reference.

Sections and headlines used throughout the present application shall not be construed as limiting.

The articles "a" and "an" are used herein to refer to one or more than one (i.e., to at least one) of the grammatical object of the article. By way of example, "a sorbent material" means one sorbent material or more than one sorbent material, unless indicated otherwise.

The term "and/or" is used herein to mean either "and" or "or" unless indicated otherwise.

The term "about" as used herein along with a recited value means the value recited and includes the range of ±10% of the recited value.

Further definitions and explanations are provided throughout the specification, as appropriate.

DETAILED DESCRIPTION

The present invention relates to filtering materials, filtering devices (8), kits and methods for removing substances from blood and/or blood components. Also, the invention relates to a blood transfusion device comprising at least one filtering device (8) according to the invention.

The blood can be whole blood. Exemplary blood components are red blood cells, platelets and plasma. Red blood cells can be provided in the form of a red cell concentrate (RCC) or as packed red cells (PRC). A preferred blood component is red blood cells, most preferably wherein the red blood cells are RCC.

Without wishing to be bound by any theory, the present inventors have found that surprisingly the materials, devices (8), methods, kits and blood transfusion systems according to the invention allow for highly efficient removal of the NO-scavengers fHb and MV, which can contribute to increased morbidity and mortality in subjects receiving transfusions, from blood and blood components. According to some embodiments, one or more additional substances can be removed from blood or blood components. The one or more additional substances can be selected from the group consisting of soluble substances, cytokines, bioactive lipids or cellular fragments.

It was found that the removal was particularly efficient in blood or blood components that have been stored prior to fHb and MV removal. Thus, the present filtering devices (8), methods, kits and blood transfusion systems are particularly suitable for the removal of fHb and MV from stored blood or blood components.

The present inventors have found that surprisingly, the present filtering materials, devices (8), methods, kits and blood transfusion systems allow for the efficient removal of fHb and MV from blood or blood components that have been stored for stored for at least 5 days, at least 10 days, at least 15 days, at least 20 days, at least 30 days, at least 35 days, at least 40 days, for 41 days or up to 42 days. Preferably, the storage occurred under blood bank conditions. In some instances, the blood or blood components have been stored for about 1 day to about 42 days, for example for about 5 days to about 35 days, for about 10 days to about 30 days, for about 30 days to about 40 days, or from about 16 days to about 25 days. Preferably, the blood or blood components have been stored under blood bank conditions.

Thus, the materials, devices (8), methods and other materials according to the invention can advantageously be used to improve the quality of stored blood and blood components, and to reduce the risk of adverse effects in the recipient of a transfusion caused by the increased contents of fHb and MV typically observed in stored blood products.

Therefore, the present filtering materials, devices (8), methods, kits and blood transfusion systems are highly useful in all procedures where the quality of blood or blood components, in particular the content of fHb and MV, is a critical parameter. Exemplary procedures are blood transfusions providing blood or blood components to subjects in need thereof, in particular blood transfusions in cardiac and paediatric surgery as well as the postoperative transfusion of non-washed autologous blood (i.e., blood that is recovered from the same individual that also is receiving the transfusion).

In addition, the filtering materials, devices (8), methods, kits and blood transfusion systems according to the present invention can be easily and safely applied to stored blood or blood components. Sample processing time, manipulation and handling are significantly reduced in comparison to the "washing" approaches of the prior art.

As an additional advantage, the filtering materials, devices (8), methods, kits and blood transfusion systems according to the present invention allow for the filtration of stored blood or a stored blood component "on demand". Thus, in contrast to methods of the prior art aiming to avoid e.g. fHb formation by treatment of blood or blood components prior to storage, the present means and methods can be selectively applied to blood or blood components after storage, as desired (e.g., as desired based on the blood's or blood component's storage time and the condition of the subject receiving the blood or blood component).

The materials, devices (8), methods, kits and blood transfusion systems of the invention are described in more detail below.

The headlines of the following sections are not to be construed as limiting to the disclosure of the invention.

Filtering Devices

The present invention provides filtering devices (8) that allow for the efficient removal of fHb and MV from blood and blood components passing through the filtering device (8).

According to some embodiments, the invention also provides filtering materials comprising or consisting of a sorbent material coupled with at least a first ligand and/or a second ligand, as further detailed below in relation with the detailed description of the filtering devices (8) according to the invention.

Housing

Typically, the filtering devices (8) according to the invention comprise a housing with an inlet and an outlet. The housing can be adapted to allow blood and blood components to pass therethrough, from the inlet to the outlet.

The housing can be made of any suitable material known in the art. Accordingly, the housing can for example be made of a soft material (such as polyvinyl chloride), a rigid material (such as polycarbonate or polyacrylate) or any combination thereof.

Also, the housing can have a length and a diameter. Length and diameter of the housing can influence liquid flow during filtration, and can also influence efficiency of substance removal from the blood or blood component passing through the filtering device (8). The present inventors have found that a ratio of housing length:housing diameter of about 2 to about 4 advantageously influences liquid flow (ml/min). Thus, according to a preferred embodiment, the ratio of housing length:housing diameter is about 2 to about 4. Preferably, the ratio is about 2 to about 3; more preferably, the ratio is about 3. It has been found that at a ratio of about 2 to about 3, optimal flow of blood components, in particular RCC, can be reached.

In order to calculate the ratio, the length of the housing is divided by the diameter of the housing. Length and diameter are determined by applying the general rules of geometry. For example, the length of the housing can be determined by determining the distance between an upper end of the housing and a lower end of the housing. The upper end of the housing can be the end where the inlet is located, and the lower end of the housing can be the end where the outlet is located. The diameter of a housing having a circular cross-section can be determined by determining the length of any straight line segment that passes through the center of the circle and whose endpoints lie on the circle. For a convex cross-sectional shape, the diameter can be determined by determining the largest distance that can be formed between two opposite parallel lines tangent to its boundary.

The filtering device (8) can allow for a flow of about 5 ml/min to about 12 ml/min, preferably from about 8 ml/min to about 11 ml/min, most preferably about 10 ml/min to about 11 ml/min, of the blood or blood component to be filtered through the filtering device (8), from the inlet port to the outlet port.

The housing can be a cartridge or column.

Sorbent Material

At least one sorbent material is located within the housing. For example, at least two, at least tree or at least four sorbent materials can be located within the housing, such as one, two, three, or four sorbent materials. However, it is preferred that two sorbent materials are located within the housing. Sometimes, a first sorbent material is located within the housing. In the alternative or in addition, a second sorbent material can be located within the housing. Typically, the second sorbent material is located in the housing in addition to the first sorbent material. However sometimes, e.g. when at least two filtering devices (8) are provided in the form of a kit, a first sorbent material may be provided in a first housing of a first filtering device (8) and a second sorbent material may be provided in a second housing of a second filtering device (8).

A "sorbent material", as used herein, can be any material (e.g. a compound or a composition) that allows for the sorption (i.e. adsorption and/or absorption, adsorption being preferred) of a substance to the material, any material that is suitable for coupling with a ligand for removing fHb and/or MV from blood or a blood component, or both.

The "substance" can be a substance that is to be removed from blood or a blood component, such as fHb, MV, other NO-scavengers, soluble substances, cytokines, bioactive lipids, cellular fragments or a combination thereof. It is preferred that the substance is fHb, MV, or both.

The sorbent materials used in the filtering devices (8) according to the present invention can be suitable for use in blood filtration applications.

For example, a sorbent material (such as the first and/or second sorbent material) used in the filtering devices (8) of the invention can comprise or essentially consist of a polymer, such as polymethacrylate, polyacrylamide, polystyrene-divinylbenzene, or a combination or co-polymer thereof. A preferred sorbent material comprises or essentially consists of polymethacrylate. A sorbent material that comprises or essentially consists of polymethacrylate sometimes is designated as being "poylmethacrylate-based" herein. The sorbent material used in the filtering devices (8) of the invention can comprise or essentially consist of methacrylate or a co-polymer thereof.

According to some embodiments, the sorbent material can be functionalized with particular chemical groups through one or more coupling reactions (for example, but not limited to, as described in Prog. Polym. Sci. 25 (2000) 711-779 or in Chem. Commun., 1998, 2275-2286, which are both incorporated herein by reference in their entirety).

By way of example and not limitation, according to a preferred embodiment, the sorbent material can be a cross-linked co-polymer of methacrylate, for example a cross-linked co-polymer of methacrylate containing oxirane groups (such as Sepabeads® EC-EP or ReliZyme™ EP403; both commercially available through Resindion SRL, Binasco (MI), Italy) Likewise, by way of example and not limitation, according to a preferred embodiment, the sorbent material can be a co-polymer of methacrylamide, N,N'-methylen-bis(acrylamide) and a monomer carrying oxirane groups, epoxide polymer-bound (such as Eupergit®; commercially available through Sigma-Aldrich Chemie GmbH, Steinheim, Germany).

The sorbent materials located within the housing can be beads or fibers, beads being preferred. At least one sorbent material (e.g., the first or the second sorbent material) can be beads, and at least one sorbent material (e.g., the first or the second sorbent material) can be fibers. In a preferred embodiment, all of the more than one sorbent materials comprise or consist of beads.

The beads can be immobilized beads. The immobilization can be effected by sinterization or by agglomeration. The immobilized beads can be placed in the housing of the filtering device (8).

The beads can have a particle diameter of about 100 µm to about 400 µm, such as about 150 µm to about 350 µm or about 200 µm to about 300 µm. A particle diameter of about 100 µm to about 200 µm is likewise preferred. According to some embodiments, the particles diameter is determined by a commercially available Malvern Instrument (Mastersizer2000, Malvern, equipped with Hydro 2000MU sampling unit and Mastersizer2000 software). The expressions "particle diameter" and "bead size" are used interchangeably herein.

Also, the beads can comprise pores. The pore size can be determined according to standard procedures known to the skilled person. According to some embodiments, the pore size is determined using a mercury porosimeter (Porosimeter demo autoPore IV 9500 V1.09 serial 413, Micromeritics Instrument Corporation; Penetrometer 10-0718 5 Bulb, 1.131 Stem, Powder; B.E.T. Gemini V—Windows—Micromeritics Instrument Corporation). The pores can have a pore size of about 50 nm to about 100 nm, for example a pore size of about 55 nm to about 100 nm, about 60 nm to about 90 nm or about 70 nm to about 80 nm. The pores can have a pore size pore size of about 60 nm to about 80 nm, more preferably about 65 nm to about 75 nm, most preferably about 70 nm.

Thus, in some embodiments the beads can have a particle diameter of about 100 µm to about 200 µm, and/or comprise pores, the pores having a pore size of about 50 nm to about 100 nm.

Also, in some embodiments the beads can have a particle diameter of about 100 µm to about 400 µm, and/or comprise pores, the pores having a pore size of about 50 nm to about 100 nm.

In embodiments where at least a first sorbent material and a second sorbent material are provided within the housing, the first sorbent material can be beads, and the second sorbent material can be fibers. Also, the first sorbent material can be fibers, and the second sorbent material can be beads.

However, it is preferred that both, the first sorbent material and the second sorbent material, are beads. The beads of the first and second sorbent materials can be the same, or can be different from each other.

For example, and without limitation, the beads of the first and second sorbent materials can differ from each other in bead size. According to a preferred embodiment, the beads of the first sorbent material can have a bead size of about 100 µm to about 200 µm, and the beads of the second sorbent material can have a bead size of about 100 µm to about 400 µm.

According to a preferred embodiment, the beads of the first sorbent material can have a pore size of about 50 nm to about 100 nm, and the beads of the second sorbent material can have a pore size of about 50 nm to about 100 nm.

In embodiments where at least a first sorbent material and a second sorbent material are provided within the housing, the first and second sorbent material can be present within the housing at a ratio of about 0.5 to about 2, such as about 0.75 to about 1.25. A ratio of about 1 is preferred. The ratio is calculated by dividing the total volume of the first type of sorbent material comprised in the housing by the total volume of the second type of sorbent material comprised in the housing. The calculation can be based on the wet volumes of the first and second sorbent materials. The inventors have found that at the above ratios, the NO-scavengers fHb and MV can be very efficiently removed from the blood or blood component to be filtered, thereby allowing to significantly improve the quality of stored blood and blood components. The effect was found to be particularly pronounced at a ratio of about 1.

Different sorbent materials (e.g., the first and the second sorbent material) can be combined or mixed outside the housing of the filtering device (8), and the combination or mixture can subsequently be filled into the housing of the filtering device (8).

In the alternative, more than one sorbent materials (e.g. at least a first sorbent material and a second sorbent material) can be filled into the housing individually and can be mixed subsequently, when already located within the housing.

Also, the more than one sorbent materials (e.g. at least a first sorbent material and a second sorbent material) can be filled into the housing individually so as to obtain different layers of sorbent material within the housing. For example, if a first sorbent material and a second sorbent material are comprised within the housing, the first sorbent material can form at least one layer within the housing, and the second sorbent material can form at least one layer within the housing. According to a preferred embodiment, the first and second sorbent materials are different from each other. According to a further preferred embodiment, the first sorbent material is coupled with at least a first ligand for the removal of fHb from blood or a blood component and the second material is coupled with at least a second ligand for the removal of fHb from blood or a blood component. Optionally, the first sorbent material is not coupled with the second ligand and/or the second sorbent material is not coupled with the first ligand. The layers formed by the first and second sorbent materials can be stacked in an alternating manner within the housing, from the inlet to the outlet. According to one embodiment, each of the layers formed by the first and second sorbent materials can have a thickness of about 0.4 cm to about 1 cm, for example about 0.5 cm, about 0.6 cm, about 0.7 cm, about 0.8 cm or about 0.9 cm. The total number of layers stacked within a housing can be at least 2, such as about 2 to about 15, for example 3, 4, 5, 6, 7, 8, 9, 10, 11, 12, 13, or 14.

Ligands

The first sorbent material located within the housing of the filtering device (8) according to the present invention is coupled with at least a first ligand. Thus the first sorbent material can be coupled with one or more ligand, such as one, at least two, at least three, at least four or at least five ligands. In preferred embodiments, the first sorbent material is coupled with one or two ligands.

In preferred embodiments, the first sorbent material and the at least one ligand coupled therewith form a resin.

The second sorbent material located within the housing of the filtering device (8) according to the present invention is coupled with at least a second ligand. Thus the second sorbent material can be coupled with one or more ligand, such as one, at least two, at least three, at least four or at least five ligands. In preferred embodiments, the second sorbent material is coupled with one or two ligands.

In preferred embodiments, the second sorbent material and the at least one ligand coupled therewith form a resin.

A "ligand", as used herein, can be any compound (e.g. a molecule) that is suitable and/or adapted for the removal of a substance from blood and/or blood components. Exemplary substances that can be removed from blood and/or blood components are fHb, MV, other NO-scavengers, soluble substances, cytokines, bioactive lipids, cellular fragments or a combination thereof. A preferred substance is fHb. Likewise, MV represents a preferred substance. Thus, a preferred ligand is a ligand for removing fHb from blood or a blood component. The expressions "first ligand" and "ligand for removing free haemoglobin" can be used interchangeably. Likewise preferred is a ligand for removing MV from blood or a blood component. A ligand can also be suitable and/or adapted for the removal of fHb and MV from blood or a blood component. Also, the expressions "second ligand" and "ligand for removing microvesicles" can be used interchangeably.

For purposes of this invention, the expression "free hemoglobin" (fHb) is defined as hemoglobin that is not encompassed within an erythrocyte. In other words, the expression encompasses hemoglobin that has been released from an erythrocyte, e.g. due to lysis or other damage occurring to the erythrocyte cell.

Also, for purposes of this invention, the term "microvesicle" (MV) is defined as a phospholipid vesicle having a size of ≤1.0 μm, e.g. from about 50 nm to 1000 nm (for example, from about 100 nm to about 900 nm, from about 200 nm to about 800 nm, from about 300 nm to about 700 nm, from about 400 nm to about 600 nm, or about 500 nm), and arising from the cellular components of blood and/or the endothelial lining of blood vessels. MV comprise fragments of the plasma membrane of the cell of origin, can expose the anionic phospholipid (PL) phosphatidylserine (PS) on the outer leaflet of their membrane, and bear surface membrane antigens reflecting their cellular origin. The MV can be an MV originating from erythrocytes.

"Coupled with", as used herein, can mean "linked with", "combined with", "connected to" "bound to" and/or "surface-modified with". Thus, the sorbent material located within the housing of the filtering device (8) according to the present invention can be coupled with, linked with, combined with, connected to bound to and/or surface-modified with at least one ligand by suitable means known to the skilled person. According to a preferred embodiment, the ligand is covalently bound to the sorbent material. It is also preferred that the sorbent material is surface-modified with the ligand.

By way of example and not limitation, a sorbent material can comprise or essentially consist of a polymethacrylate polymer comprising oxiran groups, and a ligand can comprise or essentially consist of polyacrylic acid. The oxiran groups comprised in the polymethacrylate can react with an amino compound generating an intermediate which allows for the coupling with the polyacrylic acid ligand. The ligand can be covalently bound to the sorbent material. The sorbent material can be the first sorbent material.

Likewise by way of example and not limitation, a sorbent material can comprise or essentially consist of methacrylate or a co-polymer thereof, and a ligand can have the structure R—$NH_2$, wherein R is (—$CH_2$-)n, further wherein n is an integral number from 1-5. The ligand can be covalently bound to the sorbent material. Preferably, the ligand is an ethylamino group or a methylamino group that is covalently bound to methacrylate or a co-polymer thereof. Also, it is highly preferred that the methacrylate is surface-modified with ethylamino group or methylamino groups. The sorbent material can be the second sorbent material.

Where more than the first and second sorbent material is comprised within the housing, the further sorbent materials can be coupled with the same ligand(s) or with different ligands as the first and/or second sorbent materials.

In some embodiments according to which the sorbent material (e.g., the first and/or second sorbent material) is coupled with more than one ligand, the coupling is independent. Thus, according to some embodiments, the way a sorbent material and a ligand are coupled with each other does not influence the way the sorbent material and another ligand are coupled with each other; also, the way a sorbent material and a ligand are coupled with each other does not influence the way another sorbent material and the ligand are coupled with each other.

The first sorbent material is coupled with at least a first ligand, or with at least a first and a second ligand. The first ligand and the second ligand can be the same, or can be different from each other. Typically, the first ligand and the second ligand are different from each other. For example, the first ligand and the second ligand can differ from each other in structure and/or chemical properties.

The second sorbent material is coupled with at least a second ligand, or with at least a second and a first ligand. The first ligand and the second ligand can be the same, or can be different from each other. Typically, the first ligand and the second ligand are different from each other. For example, the first ligand and the second ligand can differ from each other in structure and/or chemical properties.

The first sorbent material can be coupled with the at least first ligand by a binding reaction. The second sorbent material can be coupled with the at least second ligand by a binding reaction. According to one embodiment, the binding reaction results in covalent binding.

The "first ligand", as used herein, is a ligand that is suitable and/or adapted for removing free hemoglobin (fHb) from a sample, in particular from blood or a blood component.

According to some embodiments, the first ligand is suitable and/or adapted for removing fHb, from a sample, in particular from blood or a blood component.

The first ligand can comprise or can essentially consist of polyacrylic acid, polyacrylic ester or a combination or co-polymer thereof. According to a preferred embodiment, the first ligand comprises or essentially consists of polyacrylic acid.

The use of polyacrylic acid, polyacrylic ester or combinations or co-polymers thereof as a ligand for removing fHb offers significant advantages regarding cost and chemical stability over other ligands sometimes used for hemoglobin binding, such as adenosin-derivatives (e.g., ATP) or 2,3-diphosphoglycerate (DPG).

The "second ligand", as used herein, is a ligand that is suitable and/or adapted for removing microvesicles (MV) from a sample, in particular from blood or a blood component.

According to some embodiments, the second ligand is suitable and/or adapted for removing MV, from a sample, in particular from blood or a blood component.

The second ligand can comprise or can essentially consist of a R—$NH_2$ group. It has been found that removal of MV is most efficient if short R—$NH_2$ groups are used. Thus, the second ligand can comprise or can essentially consist of a R—$NH_2$ group wherein R is (—$CH_2$-)n, wherein n is an integral number from 1-5. Accordingly, the second ligand can comprise or can essentially consist of a —$CH_2$—$NH_2$ group, a —$CH_2$—$CH_2$—$NH_2$ group, a —$CH_2$—$CH_2$—$CH_2$—$NH_2$ group, a —$CH_2$—$CH_2$—$CH_2$—$CH_2$—$NH_2$ group or a —$CH_2$—$CH_2$—$CH_2$—$CH_2$—$CH_2$—$NH_2$ group.

Preferably, the second ligand comprises or consists of a R—$NH_2$ group, wherein R is (—$CH_2$-)n, further wherein n is 1 to 3. It is most preferred that n is 1 to 2. Hence, a highly preferred second ligand comprises or consists of a —$CH_2$—$NH_2$ group or a —$CH_2$—$CH_2$—$NH_2$ group.

The inventors have found that surprisingly, the removal of MV from blood or blood components is highly efficient when a second ligand comprising or essentially consisting of the above R—$NH_2$ group is used. The effect was particularly pronounced when a second ligand comprising or essentially consisting of a —CH$_2$—NH$_2$ group or a —CH$_2$—CH$_2$—NH$_2$ group was used.

According to a preferred embodiment of the invention, a sorbent material, such as the second sorbent material is coupled with a ligand comprising or essentially consisting of a —CH$_2$—NH$_2$ group, a ligand comprising or essentially consisting of a —CH$_2$—CH$_2$—NH$_2$ group, a ligand comprising or essentially consisting of a —CH$_2$—CH$_2$—CH$_2$—NH$_2$ group, a ligand comprising or essentially consisting of a —CH$_2$—CH$_2$—CH$_2$—CH$_2$—NH$_2$ group, a ligand comprising or essentially consisting of a —CH$_2$—CH$_2$—CH$_2$—CH$_2$—CH$_2$—NH$_2$ group, or a combination thereof.

According to a further preferred embodiment of the invention, a sorbent material, such as the second sorbent material is coupled with a ligand comprising or essentially consisting of a —CH$_2$—NH$_2$ group, and is furthermore coupled with a ligand comprising or essentially consisting of a —CH$_2$—CH$_2$—NH$_2$ group.

By way of example and not limitation, according to a preferred embodiment, a sorbent material, such as the second sorbent material can be methacrylate or a crosslinked copolymer thereof and the ligand can be —CH$_2$—NH$_2$ or —CH$_2$—CH$_2$—NH$_2$. The sorbent material can be surface-modified with the ligand. The ligand can be covalently bound to the sorbent material.

According to one embodiment, the sorbent material coupled with ligand comprises at least 0.3 milliequivalents (meq) of ligand per ml, at least 0.4 meq of ligand per ml or at least 0.5 meq of ligand per ml. The sorbent material preferably can comprise 0.3-0.4 meq of ligand per ml.

Further Features

The skilled person will realize that the filtering device (8) according to the present invention can comprise additional structural elements.

For example, the filtering device (8) according to the present invention can further comprise a net located within the housing. The net accommodates the first and/or second kind of sorbent material and allows to entrap and/or remove from the housing the first and/or second kind of sorbent material. The net can have a mesh size from about 15 µm to about 40 µm, for example from about 20 µm to about 35 µm or from about 25 µm to about 30 µm.

Also, the filtering device (8) according to the invention can comprise a pre-filter for the removal of fat and/or micro-aggregates (such as micro-aggregates of cells, in particular micro-aggregates comprising platelets) from blood or a blood component. Suitable pre-filters are known in the art and are currently used in standard transfusion procedures. The use of pre-filters is particularly preferred for the filtration of non-washed autologous blood.

The filtering devices (8) of the present invention can be adapted for connection to a container (for example a bag) comprising blood or a blood component. For example, the filtering devices (8) of the present invention can comprise connecting means, for example a spike, for connection to a container.

Also, the filtering devices (8) of the present invention can be adapted for integration into or connection with a blood transfusion system. Thus, according to one embodiment, the filtering devices (8) comprise means such as one or more tubings (7, 9), one or more connection devices (2, 3) for sterile connection to a blood transfusion system, or a combination thereof.

The filtering device (8) can be disposable.

Exemplary Preferred Embodiments

According to a preferred embodiment, the present invention provides for a filtering device (8) for removing substances from blood or a blood component, the filtering device (8) comprising: a housing having an inlet and an outlet, a first sorbent material located within the housing, wherein the first sorbent material is coupled with at least a first ligand for removing fHb, and a second sorbent material located within the housing, wherein the second sorbent material is coupled with at least a second ligand for removing microvesicles (MV) from the blood or blood component passing through the filtering device (8), from the inlet to the outlet.

It is further preferred that the first and the second sorbent materials are beads, the beads of the first sorbent material having a particle diameter of about 100 µm to about 200 µm, and comprising pores, the pores having a pore size of about 50 nm to about 100 nm, the beads of the second sorbent material having a particle diameter of about 100 µm to about 400 µm, and comprising pores, the pores having a pore size of about 50 nm to about 100 nm.

It is even more preferred that the first sorbent material coupled with the first ligand for removing fHb is polymethacrylate-based beads (for example having a bead size of about 100 µm to about 200 µm, and a pore size of about 50 nm to about 90 nm), and the first ligand for removing fHb coupled therewith comprises or essentially consists of polyacrylic acid.

It is also even more preferred that the second sorbent material coupled with the second ligand for removing MV is polymethacrylate-based beads (for example, having a bead size of about 100 µm to about 400 µm, and a pore size of about 55 nm to about 100 nm), and the second ligand comprises or essentially consists of a R—NH$_2$ group, wherein R is (—CH$_2$-)n, further wherein n is 1 to 5, preferably 1 to 3, more preferably 1-2.

Even more preferably, the polymethacrylate-based beads and the first ligand comprising or essentially consisting of polyacrylic acid coupled therewith form a resin, and the polymethacrylate-based beads and the second ligand comprising or essentially consisting of the R—NH$_2$ group coupled therewith form a resin. Most preferably, the beads are surface-modified with the ligand.

It is also preferred that bead surface area is 70-100 m$^2$/g and/or that the first and/or second sorbent material coupled with ligand comprises at least 0.3 milliequivalents (meq) of ligand per ml, such as 0.3-0.4 milliequivalents (meq) of ligand per ml.

It is most preferred that the first and second sorbent materials are present within the housing at a ratio (volume:volume) of about 1. The ratio can be calculated based on the wet volume of the first and second sorbent materials.

Blood Transfusion Systems

According to one embodiment, a blood transfusion system comprising at least one filtering device (8) according to the invention is provided.

The blood transfusion system can comprise means (2, 3) (e.g. a spike) for connection to a container comprising blood or a blood component. The blood transfusion system can comprise a dripping chamber (5). According to a preferred embodiment, the dripping chamber (5) comprises a pre-filter for removing fat and/or micro-aggregates (such as a pre-filter having a pore size of about 150 µm to about 200 µm).

Also, the blood transfusion system can comprise conduit means (4, 7, 9). The blood transfusion system can be disposable.

A non-limiting example of a blood transfusion system according to the invention is shown in FIG. 1.

The exemplary blood transfusion system comprises a cap (1), means (2) and (3) allowing for the connection of the blood transfusion system with a container comprising blood or a blood component, first conduit means (4) connecting means (2) and (3) with a dripping chamber (5) (the dripping chamber (5) optionally comprising a pre-filter for the removal of fat and/or micro-aggregates), and second conduit means (7). The blood transfusion system further comprises a filtering device (8) according to the invention, the filtering device (8) comprising a housing having an inlet and an outlet. The filtering device (8) is connected with the dripping chamber (5) through the second conduit means (7), and is connected with a means (11) allowing for the connection with an adapter (12) via a third conduit means (9). Further optional components comprised in the exemplary blood transfusion system according to FIG. 1 are a clamp (6) located on second conduit means (6) and a roller (10).

The skilled person will understand that a blood transfusion system according to the present invention can comprise, or can essentially consist of the components shown in FIG. 1 and described above. However, a blood transfusion system comprising additional elements or features is likewise contemplated by the present inventors.

Particularly preferred is a blood transfusion system according to the invention (e.g. a system as shown in FIG. 1) wherein the at least one filtering device (8) comprises a net located within a housing, the net accommodating the first and/or second sorbent material, the net being adapted for entrapping and/or removing from the housing the first and/or second sorbent material.

Methods

The present invention also provides methods for removing substances from blood or blood components. The methods can be performed using a filtering device (8) or a blood transfusion system according to the present invention. The methods can be performed ex vivo.

Accordingly, a method for removing substances from blood or a blood component is provided, the method comprising the steps: (a) providing a filtering device (8) according to the present invention or a blood transfusion system according to the present invention, and (b) allowing the blood or the blood component to pass through the filtering device (8), from the inlet to the outlet.

It is preferred that the blood component to be filtered comprises red blood cells. Even more preferably, the blood component is RCC.

The methods provided herein are particularly useful for removing fHb and MV from blood or a blood component. Hence, in a preferred embodiment, the present invention provides for a method for removing fHb and MV from blood or a blood component, the method comprising the steps: (a) providing a filtering device (8) according to the present invention or a blood transfusion system according to the present invention, and (b) allowing the blood or the blood component to pass through the filtering device (8), from the inlet to the outlet.

According to a further embodiment, the methods according to the present invention are applied to blood or blood components that have been stored.

The present inventors have found that the methods according to the present invention allow for the efficient removal of fHb and MV from blood or blood components that have been stored for at least 5 days, at least 10 days, at least 15 days, at least 20 days, at least 30 days, or at least 35 days, at least 40 days, for 41 days or up to 42 days. Preferably, the storage occurred under blood bank conditions. For example, the methods can be applied to blood or blood components that have been stored for about 1 day to about 42 days, for example for about 5 days to about 35 days, for about 10 days to about 30 days, for about 30 days to about 40 days, or from about 16 days to about 25 days, especially if the blood or blood components has been stored under blood bank conditions.

"Storage under blood bank conditions", as used herein, means that storage occurred under conditions typically used in blood banks, such as storage at a temperature of 4° C.

The present methods for removing substances from blood or blood components can result in an improved quality of blood or blood components subjected to the method. In particular, the quality of blood or blood components that have been stored for more than 15 days can be significantly improved. It has been found that the residual fHb and MV in blood or a blood component (such as RCC) can be significantly reduced in samples that have been stored for more than 15 days (e.g. for at least 16 days, for at least 20 days, for at least 30 days, for at least 35 days, for about 40 days, or for about 30 to about 40 days).

For example, residual fHb and MV can be reduced to the values detectable in blood or a blood component that has been stored under identical conditions for 15 days.

The concentration of fHb, including residual fHb, can be determined according to standard procedures known in the art. For example, the concentration of fHb can be determined using a HaemoCue Plasma Low Haemoglobin photometer (HemoCue AB) after sample centrifugation at 3000 RPM for 5 minutes, as previously described (Cardigan R., Smith K. Evaluation of the HemoCue plasma Haemoglobin analyser for assessing haemolysis in red cell concentrates during storage. Vox Sanguinis (2002); 82, 76).

Likewise, methods for determining the concentration of MV, including residual MV, have been described and are well established. For example, a flow cytometry approach based on dual labeling with Glycophorin A and Annexin V has been widely reported in the literature (Rubin O, Crettaz D, Canellini G, et al. Microparticles in stored red blood cells: an approach using flow cytometry and proteomic tools. Vox Sanguinis. 2008; 95: 288-297; Xiong Z, Oriss T B, Cavaretta J P, et al. Red cell microparticle enumeration: validation of a flow cytometric approach. Vox Sanguinis. 2012; 103, 42-48).

Preferably the methods according to the present invention allow for a removal of about 50% to about 80% (for example, of about 55% to about 75%, or of about 60% to about 70%, most preferably, of about 70% to about 80%) of the fHb comprised in the blood or blood component prior to filtration. Thus, the starting concentration of fHb in a given unit of blood or a blood component subjected to the method can be reduced significantly, and the concentration of fHb in the resultant purified blood or blood component can be about 50% to about 20% of the starting concentration. The concentration of fHb before and after the filtration can be determined using a HaemoCue Plasma Low Haemoglobin photometer (HemoCue AB) after sample centrifugation at 3000 RPM for 5 minutes, as previously described (Cardigan R., Smith K. Evaluation of the HemoCue plasma Haemoglobin analyser for assessing haemolysis in red cell concentrates during storage. Vox Sanguinis (2002); 82, 76).

Also, preferably the methods according to the present invention allow for a removal of about 50% to about 70%

(for example, of about 55% to about 65%, or of about 60%, most preferably of about 60% to about 70%) of the MV comprised in the blood or blood component prior to filtration. Thus, the starting concentration of MV in a given unit of blood or a blood component subjected to the method can be reduced significantly, and the concentration of MV in the resultant purified blood or blood component can be about 50% to about 30% of the starting concentration. The concentration of MV before and after the filtration, can be determined using dual labeling with PE-labeled anti-human Glycophorin A antibody (BD Bioscience) and Annexin V-APC (BD Bioscience), using a FACSAria III flow cytometer (Becton-Dickinson), following standard experimental procedures for FACS analysis.

Kits

The present invention also provides kits for removing substances such as fHb and MV from blood or a blood component, such as RCC.

A kit according to the present invention comprises at least one filtering device (8) and/or at least one blood transfusion system according to the present invention.

Thus, kits are provided comprising at least one, at least two, at least three, at least four, at least five or at least ten filtering devices (8) according to the present invention. The filtering devices (8) can be the same, or can be different from each other.

Preferably, the kit comprises at least two filtering devices (8) according to the present invention, wherein the filtering devices (8) are the same, or are different from each other. More preferred is that the kit comprises at least two filtering devices (8) according to the present invention, wherein the filtering devices (8) are different from each other.

The kit can comprise at least two filtering devices (8), wherein a first filtering devices (8) is adapted for the removal of fHb from blood or a blood component, and a second filtering device (8) is adapted for the removal of MV from blood or a blood component.

The filtering devices (8) comprised in a kit according to the present invention can be adapted for integration into a blood transfusion system, can be connectable to a container comprising blood or a blood component, or both.

Also, the filtering devices (8) comprised in a kit according to the present invention can be integrated in a blood transfusion system and can be connectable to a container comprising blood or a blood component.

According to one embodiment, a kit is provided, the kit comprising a first filtering device (8) for removing substances from blood or a blood component, the first filtering device (8) comprising a housing having an inlet and an outlet, and at least a first sorbent material located within the housing, wherein the first sorbent material is coupled with at least a first ligand for removing fHb from the blood or blood component passing through the first filtering device (8), from the inlet to the outlet.

The kit according to this embodiment can preferably further comprise a second filtering device (8) for removing substances from blood or a blood component according to the invention, the second filtering device (8) comprising a housing having an inlet and an outlet, and at least a second sorbent material located within the housing, wherein the second sorbent material is coupled with at least a second ligand for removing MV from the blood or blood component passing through the second filtering device (8), from the inlet to the outlet.

According to this embodiment, the first and second sorbent materials can be the same or can be different from each other.

Also, the first and second ligands can be the same or can be different from each other. It is preferred that the first and second ligands are different from each other. More preferably, the first and second sorbent materials are different from each other, and the first and second ligands are different from each other.

Optionally, the first sorbent material is not coupled with the second ligand and the second sorbent material is not coupled with the first ligand.

Furthermore, the first sorbent material located in the housing of the first filtering device (8) and the second sorbent material located in the housing of the second filtering device (8) can be comprised in the kit at a ratio (volume:volume) of about 1 to about 2. The ratio can be calculated based on the wet volume of the first and second sorbent materials.

According to a highly preferred embodiment, the kit comprises a first filtering device (8) comprising: a housing having an inlet and an outlet, a first sorbent material located within the housing, wherein the first sorbent material is coupled with at least a first ligand for removing fHb from the blood or blood component passing through the filtering device (8), from the inlet to the outlet. The kit further comprises a second filtering device (8) comprising: a housing having an inlet and an outlet, a second sorbent material located within the housing, wherein the second sorbent material is coupled with at least a second ligand for removing microvesicles (MV) from the blood or blood component passing through the filtering device (8), from the inlet to the outlet.

It is further preferred that the first and the second sorbent materials are beads, the beads of the first sorbent material having a particle diameter of about 100 µm to about 200 µm, and comprising pores, the pores having a pore size of about 50 nm to about 100 nm, the beads of the second sorbent material having a particle diameter of about 100 µm to about 400 µm, and comprising pores, the pores having a pore size of about 50 nm to about 100 nm.

It is even more preferred that the first sorbent material coupled with the first ligand for removing fHb is polymethacrylate-based beads (for example having a bead size of about 100 µm to about 200 µm, and a pore size of about 50 nm to about 90 nm), and the first ligand for removing fHb coupled therewith comprises or essentially consists of polyacrylic acid.

It is also even more preferred that the second sorbent material coupled with the second ligand for removing MV is polymethacrylate-based beads (for example, having a bead size of about 100 µm to about 400 µm, and a pore size of about 55 nm to about 100 nm), and the second ligand comprises or essentially consists of a R—NH$_2$ group, wherein R is (—CH$_2$-)n, further wherein n is 1 to 5, preferably 1 to 3, more preferably 1-2.

Even more preferably, the polymethacrylate-based beads and the first ligand comprising or essentially consisting of polyacrylic acid coupled therewith form a resin, and the polymethacrylate-based beads and the second ligand comprising or essentially consisting of the R—NH$_2$ group coupled therewith form a resin. Most preferably, the beads are surface-modified with the ligand.

It is also preferred that bead surface area is 70-100 m$^2$/g and/or that the first and/or second sorbent material coupled with ligand comprises at least 0.3 milliequivalents (meq) of ligand per ml, such as 0.3-0.4 milliequivalents (meq) of ligand per ml.

It is most preferred that the first and second sorbent materials are present within the kit at a ratio (volume:

volume) of about 1. The ratio can be calculated based on the wet volume of the first and second sorbent materials.

EXAMPLES

The invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

The capacity of a filtering device (8) and a blood transfusion system according to the invention to remove free hemoglobin (fHb) and microvesicles (MV) from stored red cell concentrate (RCC) was tested under controlled conditions and with known starting concentrations of fHb and MV.

The filtering device (8) used comprised a housing having the following dimensions: 8 cm length and 2.6 cm diameter, (ratio length:diameter about 3). Polymethacrylate-based beads coupled with polyacrylic acid (bead size 100 µm to 200 µm, pore size 50 nm to 90 nm) were located within the housing for removing fHb from the stored RCC. Also, beads (beads size 100 µm to 400 µm; pore size 55 nm to 100 nm; surface area: 70 $m^2/g$ to 100 $m^2/g$; 0.3 meq/ml to 0.4 meq/ml) having a metacrylate-based surface coupled with short chain amino groups of the general formula R—$NH_2$, wherein R is (—$CH_2$-)n, with n=1-2) were located within the housing and were used for removing MV from the stored RCC.

In preparation of the experiment, 22 ml of the polymethacrylate-based beads coupled with polyacrylic acid and 22 ml of the beads having a methacrylate-based surface coupled with short chain amino groups dissolved in physiological saline solution were mixed together and then filled into the housing of the filtering device (8).

The filtering device (8) was then connected to a blood transfusion device. The blood transfusion device further comprised a spike for connection to a container comprising the RCCs, a dripping chamber (5) comprising a 150 µm to 200 µm pre-filter for micro-aggregates, and conduit means (4, 7, 9), as appropriate. Reference is made to FIG. 1.

Priming was achieved with 250 ml of physiological saline solution in order to remove air.

RCCs stored under standard blood bank conditions (at 4° C.) for 30 days to 40 days were leuko-depleted and the initial concentrations of fHb and MV in the samples were determined. Free haemoglobin was measured by HaemoCue Plasma Low Haemoglobin photometers (HemoCue AB) after sample centrifugation at 3000 RPM×5 minutes; MVs were measured by a flow cytometry approach based on dual labeling with Glycophorin A, Annexin V. The samples were spiked with human fHb in order to obtain samples with known precise fHb starting concentrations of 450 mg/dl, 460 mg/dl or 1020 mg/dl. The starting concentrations of MV determined in the samples were in the range of 60.000 MV/µl-80.000 MV/µl prior to filtration.

The RCC volume used per test was in the range of 240 ml to 260 ml and the hematocrit was between 55% and 60%.

For each test, the container with stored RCC was connected to the system and the filtration was started. The filtering device (8) was inverted during the whole filtration and flow was controlled using a roller to reach a flow value of 10 ml/min. Initially, physiological saline solution used to prime the system was eluted and was discharged. Then, purified RCC was collected and analyzed.

The concentrations for fHb and MV were determined after filtration.

Results are shown in Table 1.

TABLE 1

|  | Starting fHb (mg/dl) | Residual fHb (mg/dl) | fHb removal (%) | Flow (ml/min) | MV removal (%) |
|---|---|---|---|---|---|
| Test 1 | 450 | 90 | 80% | 10.7 | 50% |
| Test 2 | 460 | 140 | 70% | 10.2 | 70% |
| Test 3 | 1020 | 440 | 57% | 10.7 | — |

The results depicted in Table 1 clearly show that filtering device (8)s and blood transfusion systems of the present invention are highly efficient in removing fHb and also MV from stored blood components, while at the same time allowing for excellent flow rates that fit typical bedside transfusion times.

Example 2

The experiment was performed as described above for Example 1, but without the initial priming of the system with physiological saline solution. Instead, the conduit means (4, 7) located upstream of the filtering device (8), i.e. between filtering device (8) and spike for connection to the container with RCC, was filled with RCC in order to remove air and then was connected to the filtering device (8). Filtration was performed as for Example 1. The results are shown in Table 2.

TABLE 2

|  | Starting fHb (mg/dl) | Residual fHb (mg/dl) | fHb removal (%) | Flow (ml/min) | MV removal (%) |
|---|---|---|---|---|---|
| Test 4 | 460 | 145 | 68% | 9.6 | 65% |

Thus, even without the use of physiological saline solution to prime the system, fHb and MV are efficiently removed.

Example 3

The effect of different sorbent materials coupled with linkers on the removal of MV from stored blood components (RCC) was evaluated.

Tested sorbent materials coupled with linkers were cross-linked copolymers of methacrylate-based beads, which were surface modified by coupling with amino groups with different chain lengths.

The amino groups coupled to the sorbent material had the general formula R—$NH_2$, with R=(—$CH_2$-)n. For amino groups of the general formula R—$NH_2$, with R=(—$CH_2$-)n and n=1 or 2, R was designated as "short", while for amino groups of the general formula R—$NH_2$, with R=(—$CH_2$-)n and n=3-5, R was designated as "medium". For amino groups of the general formula R—$NH_2$, with R=(—$CH_2$-)n and n>5, R was designated as "long".

The bead size was in the range 100 µm to 400 µm. The Ion Exchange Capacity (IEC) was in the range 0.3 meq/g to 0.9 meq/g.

A scale down experiment was performed in order to use one RCC unit (corresponding to a volume of 250-320 ml depending on volume donation and procedure) with a known amount of starting MVs.

Tested sorbent materials coupled with linkers were cross-linked copolymers of methacrylate-based beads, which were surface-modified by coupling with short (Test 5), medium (Test 6) or long (Test 7) amino groups.

A leuko-reduced RCC unit, stored under standard blood bank conditions (at 4° C.) for 41 days, was aliquoted into three samples. The RCC volume was 80 ml for each aliquot and the hematocrit was 58%.

Microvesicles were measured using a Flow Cytometer-based method. Different specific markers such as PE anti-human Glycophorin A antibody (BD Bioscience) and Annexin V-APC (BD Bioscience) were used for MV detection and identification. TruCount tubes (BD Bioscience) containing a standardize number of fluorescent beads, were used for the absolute countings.

The volume of sorbent material coupled with a linker filled into the respective filtering device (8) was calculated to provide a comparable ion exchange capacity for Tests 5-7. The volume applied to the filtering device (8)s was between 6 and 9 ml.

For each test, the filtering device (8) (ratio length:diameter of about 3) was connected to the system and primed with 150 ml of NaCl 0.9% (physiological saline solution).

The saline then was removed from the system and the saline bag was removed and replaced by an RCC bag. The upstream tube was filled with RCC, in order to remove air and then connected to the filtering device (8). Then, filtration was started. The cartridge was kept in inverted position during the whole filtration and flow was controlled just by the dimension of the beads.

MVs were measured before and after filtration. Table 3 shows the MV removal (%) achieved for the above-described beads coupled with amino acid groups of different chain lengths.

TABLE 3

| | $R-NH_2$ | MVs removal (%) |
|---|---|---|
| Test 5 | R = short (1-2) | 50-60% |
| Test 6 | R = medium (3-5) | 15% |
| Test 7 | R = long (>5) | No removal |

The results depicted in Table 3 clearly show that the chain length of amino groups affects MV removal from blood or blood components, such as RCC. Removal is excellent for short chain lengths. Removal is reduced for medium chain lengths. No removal of MV from the test sample was observed for long chain lengths.

The sorbent material coupled with a linker used in Test 5 showed an excellent capacity for the removal of MV, and has been used in a scale up experiment together with the resin for fHb removal (see also Example 1).

The invention claimed is:

1. A filtering device for removing free hemoglobin (fHb) and microvesicles (MV) from blood or a blood component, the filtering device comprising:
    a housing having an inlet and an outlet,
    a first sorbent material and a first ligand covalently bonded to said first sorbent, wherein said first sorbent is located within the housing, and
    a second sorbent material and a second ligand covalently bonded to said second sorbent, wherein said second sorbent is also located within the housing,
    wherein the first ligand is selected and targeted for removing free hemoglobin (fHb) and the second ligand is selected and targeted for removing microvesicles (MV) from the blood or blood component passing through the filtering device, from the inlet to the outlet,
    wherein the first and second ligand are different from each other, wherein the first ligand for removing fHb comprises polyacrylic acid, polyacrylic ester or a combination or co-polymer thereof and the second ligand for removing MV comprises at least one $R-NH_2$ group, wherein R is $(-CH_2-)_n$, wherein n is 1-5, and
    wherein the first and second sorbent materials are the same or are different from each other.

2. The filtering device of claim 1, wherein the first sorbent material is not coupled with the second ligand and the second sorbent material is not coupled with the first ligand.

3. The filtering device according to claim 1,
    wherein the first and/or second sorbent material comprises a polymer, the polymer comprising polymethacrylate, polyacrylamide, polystyrene-divinylbenzene, or a combination or co-polymer thereof.

4. The filtering device according to claim 1,
    wherein the first sorbent material is coupled with the at least first ligand by a binding reaction, and/or wherein the second sorbent material is coupled with the at least second ligand by a binding reaction.

5. The filtering device according to claim 1,
    wherein the first and/or second sorbent material is selected from the group consisting of beads and fibers.

6. The filtering device according to claim 5,
    wherein the beads have a particle diameter of about 100 μm to about 400 μm; and/or
    wherein the beads comprise pores, the pores having a pore size of about 50 nm to about 100 nm.

7. The filtering device according to claim 1,
    the filtering device comprising a first sorbent material that is beads having a particle diameter of about 100 μm to about 200 μm, and comprising pores having a pore size of about 50 nm to about 100 nm, and/or
    the filtering device comprising a second sorbent material that is beads having a particle diameter of about 100 μm to about 400 μm, and comprising pores, the pores having a pore size of about 50 nm to about 100 nm.

8. The filtering device according to claim 1,
    wherein the first sorbent material and the second sorbent material are provided within the housing at a ratio (volume:volume) of about 0.5 to about 2.

9. The filtering device according to claim 1,
    wherein the first sorbent material forms at least one layer within the housing, and the second sorbent material forms at least one layer within the housing, and wherein the layers formed by the first and second sorbent materials are stacked; or
    wherein the first sorbent material and the second sorbent material are substantially equally dispersed within the housing.

10. The filtering device according to claim 1,
    wherein the filtering device is adapted for integration into a blood transfusion system, and/or
    wherein the filtering device is connectable to a container comprising blood or a blood component.

11. The filtering device according to claim 1, wherein the housing has a length and a diameter, wherein the ratio of length:diameter is from about 2 to about 4, optionally wherein the housing is a column, or is a cartridge.

12. The filtering device according to claim 1, further comprising a net located within the housing, the net accommodating the first and/or second sorbent material, the net being adapted for entrapping and/or removing from the housing the first and second sorbent material.

13. The filtering device according to claim 1, wherein the blood component comprises red blood cells.

14. A blood transfusion system comprising at least one filtering device according to claim 1.

15. A method for removing free hemoglobin (fHb) and microvesicles (MV) from blood or a blood component, the method comprising the steps:
(a) providing a filtering device comprising a housing having an inlet and an outlet,
a first sorbent material coupled with at least a first ligand located within the housing, and a second sorbent material coupled with at least a second ligand located within said housing,
wherein the first ligand is for removing free hemoglobin (fHb) and the second ligand is for removing microvesicles (MV) from the blood or blood component passing through the filtering device, from the inlet to the outlet,
wherein the first and second ligand are different from each other,
wherein the first ligand for removing fHb comprises polyacrylic acid, polyacrylic ester or a combination or co-polymer thereof and the second ligand for removing MV comprises at least one R—$NH_2$ group, wherein R is (—$CH_2$—)$_n$, wherein n is 1-5,
wherein the first and second sorbent materials are the same or are different from each other,
(b) allowing the blood or blood component to pass through the filtering device, from the inlet to the outlet.

16. The method according to claim 15, wherein the blood component comprises red blood cells.

17. The method according to claim 15, wherein the blood or blood component has been stored prior to filtration.

18. A kit comprising for removing free hemoglobin (fHb) and microvesicles (MV) from blood or a blood component, the kit comprising:
a first filtering device for removing free hemoglobin (fHb) from blood or a blood component, the first filtering device comprising a housing having an inlet and an outlet, and at least a first sorbent material located within the housing,
wherein the first sorbent material is covalently bonded to a first ligand selected and targeted for removing fHb from the blood or blood component passing through the first filtering device, from the inlet to the outlet, wherein said first ligand for removing fHb comprises polyacrylic acid, polyacrylic ester or a combination or co-polymer thereof, and
a second filtering device for removing substances from blood or a blood component, the second filtering device comprising a housing having an inlet and an outlet, and at least a second sorbent material located within the housing,
wherein the second sorbent material is covalently bonded to a second ligand selected and targeted for removing MV from the blood or blood component passing through the second filtering device, from the inlet to the outlet, wherein said second ligand for removing MV comprises at least one R—$NH_2$ group, wherein R is (—$CH_2$—)$_n$, wherein n is 1-5,
wherein the first and second ligand are different from each other, and
wherein the first and second sorbent material are the same or are different from each other,
optionally wherein the first sorbent material is not coupled with the second ligand and the second sorbent material is not coupled with the first ligand.

19. The kit according to claim 18,
wherein the first and/or second filtering device is adapted for integration into a blood transfusion system, and/or
wherein the first and/or second filtering device is connectable to a container comprising blood or a blood component.

20. The kit according to claim 18, wherein the first filtering device and the second filtering device are integrated in a blood transfusion system and are connectable to a container comprising blood or a blood component.

21. The filtering device according to claim 1, wherein the first and/or second sorbent material is beads, wherein further the beads are immobilized by sinterization or by agglomeration.

22. The filtering device of claim 1 wherein n is 1-3.

23. The filtering device of claim 1 wherein n is 1-2.

24. The filtering device of claim 3 wherein the polymer is polymethacrylate.

25. The filtering device of claim 8 wherein the ratio (volume:volume) is about 1.

26. The filtering device of claim 11 wherein the ratio of length:diameter is from about 2 to about 3.

27. The filtering device of claim 13 wherein wherein the blood component is red cell concentrate (RCC).

28. The method of claim 15 wherein n is 1-3.

29. The method of claim 15 wherein n is 1-2.

30. The method of claim 16 wherein the blood component is red cell concentrate (RCC).

31. The kit of claim 18 wherein n is 1-3.

32. The kit of claim 18 wherein n is 1-2.

* * * * *